(12) United States Patent
Yoshikawa et al.

(10) Patent No.: US 10,500,579 B2
(45) Date of Patent: *Dec. 10, 2019

(54) METATITANIC ACID PARTICLE, COMPOSITION FOR FORMING PHOTOCATALYST, AND PHOTOCATALYST

(71) Applicant: FUJI XEROX CO., LTD., Tokyo (JP)

(72) Inventors: Hideaki Yoshikawa, Kanagawa (JP);
Yasunobu Kashima, Kanagawa (JP);
Takeshi Iwanaga, Kanagawa (JP);
Sakae Takeuchi, Kanagawa (JP);
Hiroyoshi Okuno, Kanagawa (JP)

(73) Assignee: FUJI XEROX CO., LTD., Minato-ku, Tokyo (JP)

( * ) Notice: Subject to any disclaimer, the term of this patent is extended or adjusted under 35 U.S.C. 154(b) by 18 days.

This patent is subject to a terminal disclaimer.

(21) Appl. No.: 15/891,497

(22) Filed: Feb. 8, 2018

(65) Prior Publication Data
US 2018/0311656 A1 Nov. 1, 2018

(30) Foreign Application Priority Data
Apr. 26, 2017 (JP) .................................. 2017-087540

(51) Int. Cl.
| | | |
|---|---|---|
| *B01J 31/38* | (2006.01) | |
| *B01J 21/06* | (2006.01) | |
| *B01J 35/00* | (2006.01) | |
| *B01J 37/00* | (2006.01) | |
| *B01J 37/03* | (2006.01) | |
| *B01J 37/34* | (2006.01) | |
| *B01J 31/06* | (2006.01) | |
| *G01N 21/31* | (2006.01) | |

(52) U.S. Cl.
CPC ............ *B01J 31/38* (2013.01); *B01J 21/063* (2013.01); *B01J 31/069* (2013.01); *B01J 35/002* (2013.01); *B01J 35/004* (2013.01); *B01J 37/0045* (2013.01); *B01J 37/033* (2013.01); *B01J 37/344* (2013.01); *G01N 2021/3155* (2013.01)

(58) Field of Classification Search
CPC ........ B01J 31/38; B01J 21/063; B01J 35/002; B01J 35/004; B01J 37/0045; B01J 37/033; B01J 37/344
See application file for complete search history.

(56) References Cited

U.S. PATENT DOCUMENTS

| | | | |
|---|---|---|---|
| 5,411,761 A | 5/1995 | Inokuchi et al. | |
| 5,922,500 A * | 7/1999 | Iida ..................... | G03G 9/09708 428/405 |
| 5,965,312 A | 10/1999 | Nakazawa et al. | |
| 6,171,747 B1 | 1/2001 | Sugizaki et al. | |
| 6,235,270 B1 | 5/2001 | Ishii et al. | |
| 7,090,823 B1 | 8/2006 | Liu | |
| 7,211,543 B2 | 5/2007 | Nakabayash et al. | |
| 7,959,980 B2 | 6/2011 | Nakajima et al. | |
| 10,155,220 B2 * | 12/2018 | Kashima ................ | B01J 35/004 |
| 10,183,275 B2 | 1/2019 | Okuno et al. | |
| 2004/0248075 A1 | 12/2004 | Yamaguchi et al. | |
| 2006/0009351 A1 | 1/2006 | Iwamoto et al. | |
| 2006/0162617 A1 | 7/2006 | Tanaka et al. | |
| 2007/0248831 A1 | 10/2007 | Nishihara et al. | |
| 2007/0269732 A1 | 11/2007 | Matsumura et al. | |
| 2008/0268268 A1 | 10/2008 | Masaki et al. | |
| 2010/0279118 A1 | 11/2010 | Hempenius | |
| 2011/0159109 A1 | 6/2011 | Lee et al. | |
| 2012/0040194 A1 | 2/2012 | Kanai et al. | |
| 2012/0122668 A1 | 5/2012 | Celiker et al. | |
| 2013/0164444 A1* | 6/2013 | Tokumitsu ........... | C01G 23/053 427/219 |
| 2017/0218204 A1 | 8/2017 | Edwards et al. | |
| 2017/0252736 A1 | 9/2017 | Hirose et al. | |
| 2017/0253621 A1 | 9/2017 | Yoshikawa et al. | |
| 2018/0161763 A1 | 6/2018 | Iwanaga et al. | |
| 2018/0161764 A1 | 6/2018 | Okuno et al. | |
| 2018/0161765 A1 | 6/2018 | Kashima et al. | |
| 2018/0162887 A1 | 6/2018 | Okuno et al. | |
| 2018/0280953 A1 | 10/2018 | Iwanaga et al. | |
| 2018/0311643 A1 | 11/2018 | Okuno et al. | |

FOREIGN PATENT DOCUMENTS

| | | | |
|---|---|---|---|
| CN | 102317069 | A | 1/2012 |
| JP | 5-221640 | A | 8/1993 |
| JP | 8-269359 | A | 10/1996 |
| JP | 2001-81394 | A | 3/2001 |
| JP | 2001-269573 | A | 10/2001 |
| JP | 2004-115541 | A | 4/2004 |
| JP | 2006-21112 | A | 1/2006 |
| JP | 2006-116462 | A | 5/2006 |
| JP | 2007-016111 | A | 1/2007 |

(Continued)

OTHER PUBLICATIONS

Office Action dated Jan. 25, 2019 in U.S. Appl. No. 15/687,621.

(Continued)

*Primary Examiner* — Cam N. Nguyen
(74) *Attorney, Agent, or Firm* — Sughrue Mion, PLLC

(57) ABSTRACT

A metatitanic acid particle includes a metal compound having a titanium metal atom and a carbon atom, and being bonded to a surface of the particle via an oxygen atom, wherein an element ratio (C/Ti) between carbon and titanium on the surface is in a range of 0.2 to 1.1 and the metatitanic acid particle has an absorption at a wavelength of each of 450 nm and 750 nm in a visible absorption spectrum.

11 Claims, No Drawings

(56) References Cited

FOREIGN PATENT DOCUMENTS

| | | |
|---|---|---|
| JP | 2008-212841 A | 9/2008 |
| JP | 2010-006629 A | 1/2010 |
| JP | 2010-78861 A | 4/2010 |
| JP | 2013-249229 A | 12/2013 |
| JP | 2014-128768 A | 7/2014 |
| JP | 2014-188417 A | 10/2014 |
| JP | 2016-148786 A | 8/2016 |
| WO | 2015/177562 A1 | 11/2015 |

OTHER PUBLICATIONS

Office Action dated Mar. 19, 2019 in U.S. Appl. No. 15/484,407.
Office Action dated May 22, 2019 in U.S. Appl. No. 15/666,861.
Office Action dated May 15, 2019 in Chinese Application No. 201610681883.6.
Office Action dated May 15, 2019 in Chinese Application No. 201610803424.0.
Office Action dated Jun. 20, 2017 in Japanese Application No. 2017-041023.
Office Action dated Jun. 20, 2017 in Japanese Application No. 2017-041024.
Office Action dated Dec. 7, 2016 in U.S. Appl. No. 15/208,278.
Office Action dated Apr. 20, 2017 in U.S. Appl. No. 15/208,278.
Office Action dated Oct. 26, 2017 in U.S. Appl. No. 15/208,278.
Office Action dated Mar. 16, 2018 in U.S. Appl. No. 15/208,278.
Office Action dated Aug. 7, 2018 in U.S. Appl. No. 15/208,278.
Office Action dated Apr. 29, 2019 in U.S. Appl. No. 15/208,278.
Office Action dated Dec. 7, 2016 in U.S. Appl. No. 15/212,021.
Office Action dated Apr. 20, 2017 in U.S. Appl. No. 15/212,021.
Office Action dated Oct. 25, 2017 in U.S. Appl. No. 15/212,021.
Office Action dated Mar. 8, 2018 in U.S. Appl. No. 15/212,021.
Office Action dated Aug. 13, 2018 in U.S. Appl. No. 15/212,021.
Office Action dated Apr. 29, 2019 in U.S. Appl. No. 15/212,021.
Office Action dated Jan. 25, 2019 in U.S. Appl. No. 15/672,497.
Office Action dated Apr. 26, 2019 in U.S. Appl. No. 15/903,093.
Office Action dated Sep. 27, 2017 in U.S. Appl. No. 15/491,030.
Office Action dated Apr. 20, 2018 in U.S. Appl. No. 15/491,030.
Office Action dated Jul. 2, 2019 in U.S. Appl. No. 15/484,407.
Office Action dated Jul. 17, 2019 in U.S. Appl. No. 15/672,497.
Office Action dated Jul. 22, 2019 in U.S. Appl. No. 15/687,621.

* cited by examiner

METATITANIC ACID PARTICLE, COMPOSITION FOR FORMING PHOTOCATALYST, AND PHOTOCATALYST

CROSS-REFERENCE TO RELATED APPLICATIONS

This application is based on and claims priority under 35 USC 119 from Japanese Patent Application No. 2017-087540 filed Apr. 26, 2017.

BACKGROUND

Technical Field

The present invention relates to a metatitanic acid particle, a composition for forming a photocatalyst, and a photocatalyst.

SUMMARY

According to an aspect of the invention, there is provided a metatitanic acid particle including:

a metal compound having a titanium metal atom and a carbon atom, and being bonded to a surface of the particle via an oxygen atom, wherein an element ratio (C/Ti) between carbon and titanium on the surface is in a range of 0.2 to 1.1; and the metatitanic acid particle has an absorption at a wavelength of each of 450 nm and 750 nm in a visible absorption spectrum.

DETAILED DESCRIPTION

Hereinafter, an exemplary embodiment which is an example of the invention will be described.

Metatitanic Acid Particle

Regarding a metatitanic acid particle according to the exemplary embodiment, a metal compound which includes a titanium atom and a hydrocarbon group is bonded to the surface thereof via an oxygen atom. The metatitanic acid particle absorbs light having a wavelength of 450 nm and light having a wavelength of 750 nm in a visible absorption spectrum. An element ratio C/Ti between carbon C and titanium Ti on the surface thereof is 0.2 to 1.1.

The metatitanic acid particle according to the exemplary embodiment is suitably used as a photocatalyst.

The metatitanic acid particle according to the exemplary embodiment has the above configuration, and thus shows a high photocatalyst function even in the visible light region. The reason therefor is supposed as follows.

Firstly, an untreated titanium oxide particle which is used as a photocatalyst in the related art absorbs ultraviolet light, and thus shows a photocatalyst function (photocatalyst activity). Thus, the untreated titanium oxide particle shows the photocatalyst function during a daytime on a sunny day on which ultraviolet light is ensured, but the photocatalyst function is degraded to insufficient levels during a nighttime or in the shade. For example, in a case where the untreated titanium oxide particle is used as an exterior wall material, a difference in stain resistance may often occur between a sunny place and a shade place. In a case where the untreated titanium oxide particle is used in an air cleaner, a water purifier, or the like, an additional mounting space for example, mounting a black light or the like which functions as a light source of an ultraviolet ray in the device may be required.

Recently, titanium oxide particles which show the photocatalyst function (photocatalyst activity) by absorbing visible light are also known. For example, a titanium oxide particle obtained by adhering a different type of metal (iron, copper, platinum, and the like) to titanium oxide, a titanium oxide particle obtained by doping a nitrogen element, a sulfur element, and the like are known as a visible light-absorption type titanium oxide particle.

On the other hand, a metatitanic acid particle which shows the high photocatalyst function even in a visible light region is required.

With respect to this, regarding to the metatitanic acid particle according to the exemplary embodiment, a metal compound which includes a titanium atom and a hydrocarbon group is bonded to the surface thereof via an oxygen atom. The metatitanic acid particle absorbs light having a wavelength of each of 450 nm and 750 nm in the visible absorption spectrum. The element ratio C/Ti between carbon C and titanium Ti on the surface thereof is 0.2 to 1.1.

The metatitanic acid particle according to the exemplary embodiment is obtained, for example, in a manner as follows. The untreated metatitanic acid particle is subjected to a surface treatment with a metal compound which includes a titanium atom and a hydrocarbon group. Then, at least a portion of the hydrocarbon group is oxidized by a heating treatment, and thus is changed to a C—O bond or a C═O bond. The detailed mechanism is not clear. However, it is supposed as follows. That is, a structure in which a metal compound in which carbon atoms are adequately oxidized, an oxygen atom, and a titanium atom are joined in sequence by a covalent bond is provided on the surface of the metatitanic acid particle. Thus, the surface of the metatitanic acid particle shows light absorbency at wavelengths of 450 nm and 750 nm, and the metatitanic acid particle shows visible light responsiveness.

The element ratio C/Ti on the surface of the metatitanic acid particle is 0.2 to 1.1, and thus an amount of carbon in the hydrocarbon group and the like on the surface of the metatitanic acid particle is adequate. Light having a wavelength of each of 450 nm and 750 nm is sufficiently absorbed, and the high photocatalyst function is shown in the visible light region.

Specifically, since the element ratio C/Ti is in the above range, the adequate amount of the metal compound is bonded to the surface, and thus the sufficient amount of light is absorbed at wavelengths of 450 nm and 750 nm and the photocatalyst function in the visible light region is improved, in comparison to a case where the element ratio C/Ti is smaller than the above range. Since the element ratio C/Ti is in the above range, reduction of the exposed amount of an active portion of metatitanic acid and decomposition of the hydrocarbon group caused by an excess amount of the metal compound bonded to the surface are prevented and the photocatalyst function in the visible light region is easily obtained, in comparison to a case where the element ratio C/Ti is greater than the above range.

From the above reasons, it is supposed that the metatitanic acid particle according to the exemplary embodiment shows the high photocatalyst function even in the visible light region, with the above configuration.

The metal compound which is bonded to the surface of the metatitanic acid particle according to the exemplary embodiment via an oxygen atom thereof is preferably at least one of a metal compound formed only by a titanium atom, a carbon atom, a hydrogen atom, and an oxygen atom and a metal compound formed by a titanium atom, a carbon atom, a hydrogen atom, an oxygen atom, and a phosphorus atom, from a viewpoint of more easily showing the visible light responsiveness. The metal compound formed only by a titanium atom, a carbon atom, a hydrogen atom, and an oxygen atom is more preferable.

As the metal compound which is bonded to the surface of the metatitanic acid particle according to the exemplary embodiment via an oxygen atom thereof, a compound which is bonded to the surface of the metatitanic acid particle via an oxygen atom O which is directly bonded to a titanium atom Ti, that is, a compound which is bonded to the surface of the metatitanic acid particle by a covalent bond of Ti—O—Ti is preferable among metal compounds, from a viewpoint of more easily showing the visible light responsiveness.

Regarding the metatitanic acid particle according to the exemplary embodiment, from a viewpoint of more easily showing the visible light responsiveness, it is preferable that a metal compound which has a titanium atom and a hydrocarbon group bonded to the titanium atom via an oxygen atom is bonded to the surface of the metatitanic acid particle with an oxygen atom interposed therebetween. That is, it is preferable that a structure (C—O—Ti—O—Ti) in which a carbon atom C in the hydrocarbon group, an oxygen atom O, a titanium atom Ti in the metal compound, an oxygen atom O, and a titanium atom Ti in the metatitanic acid particle are joined in sequence by a covalent bond is provided on the surface of the metatitanic acid particle. It is supposed that the above structure is provided and the adequate amount of carbon atoms C is oxidized, and thus the surface of the metatitanic acid particle shows light absorbency at wavelengths of 450 nm and 750 nm, and the metatitanic acid particle shows more visible light responsiveness.

The metatitanic acid particle according to the exemplary embodiment is also excellent from a viewpoint described below, in addition to a point of showing the high photocatalyst function even in the visible light region.

Generally, an untreated metatitanic acid particle has a low degree of freedom for controlling a particle diameter, particle diameter distribution, and a shape of a particle, and has high particle aggregation. Thus, the metatitanic acid particle does not have favorable dispersibility in a resin or a liquid, and there is a tendency that (1) showing of the photocatalyst function is difficult, (2) uniformity of a coated film formed with a coating liquid is low, and (3) transparency of a film and the like is low.

However, the metatitanic acid particle according to the exemplary embodiment has favorable dispersibility because a hydrocarbon group derived from the metal compound is provided on the surface of the metatitanic acid particle. Thus, a coated film is substantially uniformly formed, and light hits the metatitanic acid particle with high efficiency, and thus the photocatalyst function is easily shown. Transparency of a film and the like, uniformity of a coated film of a coating liquid are improved, and design properties are held. As a result, for example, when a coating material including the metatitanic acid particle is applied onto the surface of an outer wall material, a plate, a pipe, or nonwoven fabric (non-woven fabric of ceramic and the like), aggregation of metatitanic acid particles or an occurrence of coating defects is prevented, and the photocatalyst function is easily shown for a long term.

Details of the metatitanic acid particle according to the exemplary embodiment will be described below.

Preferably, the metatitanic acid particle according to the exemplary embodiment is a metatitanic acid particle obtained in a manner that an untreated metatitanic acid particle is subjected to a surface treatment with a metal compound which includes a titanium atom and a hydrocarbon group, and then at least a portion of the hydrocarbon group is oxidized by a heating treatment. In this disclosure, the metal compound which includes a titanium atom and a hydrocarbon group is also simply referred to as "a metal compound".

Untreated Metatitanic Acid Particle

In this disclosure, a metatitanic acid particle which is not subjected to a surface treatment with a metal compound is referred to as "an untreated metatitanic acid particle". The untreated metatitanic acid particle (metatitanic acid particle which is a target of a surface treatment) refers to a particle of titanic acid which satisfies n=1 among titanic acid hydrates $TiO_2 \cdot nH_2O$.

The untreated metatitanic acid particle in the exemplary embodiment is a metatitanic acid particle which is not subjected to a surface treatment with a metal compound, and includes a metatitanic acid particle which is subjected to other surface treatments. However, it is preferable that the metatitanic acid particle according to the exemplary embodiment is a metatitanic acid particle subjected to a surface treatment with only a metal compound.

A preparing method of the untreated metatitanic acid particle is not particularly limited. However, a chlorine method (vapor phase method), and a sulfuric acid method (liquid phase method) are exemplified.

An example of the chlorine method (vapor phase method) is as follows. Firstly, rutile ore is caused to react with coke and chlorine. After the reactant is exposed to gaseous titanium tetrachloride once, cooling is performed, thereby a titanium tetrachloride liquid is obtained. Then, titanium tetrachloride is dissolved in water, and hydrolysis is caused while a strong base is put into the water in which titanium tetrachloride is dissolved. Thus, an untreated metatitanic acid [titanium oxyhydroxide $(TiO(OH)_2)$] particles are obtained.

An example of the sulfuric acid method (liquid phase method) is as follows. Firstly, ilmenite ore ($FeTiO_3$) or titanium slag is dissolved in concentrated sulfuric acid, and an iron component which is an impurity is separated in a form of iron sulfate ($FeSO_4$), thereby titanium oxysulfate ($TiOSO_4$) is obtained (titanyl sulfate solution). Then, titanium oxysulfate ($TiOSO_4$) is subjected to hydrolysis, and thus an untreated metatitanic acid [titanium oxyhydroxide $(TiO(OH)_2)$] particle is obtained.

Metal Compound

The "metal compound including a titanium atom and a hydrocarbon group" which is provided on the surface of the metatitanic acid particle according to the exemplary embodiment is derived from a metal compound used when a surface treatment is performed on the metatitanic acid particle.

A metal compound which includes a titanium atom and a hydrocarbon group which is bonded to the titanium atom with an oxygen atom interposed (more preferably, with only one oxygen atom interposed) is preferable as the metal compound used when a surface treatment is performed on the metatitanic acid particle. In a case where the metal compound includes plural hydrocarbon groups, at least one hydrocarbon group is preferably bonded to the titanium atom of the metal compound with an oxygen atom interposed (more preferably with only one oxygen atom interposed) between the hydrocarbon group and the titanium atom, from a viewpoint of showing the high photocatalyst function and improving dispersibility.

The hydrocarbon group may be bonded to the titanium atom of the metal compound with a linking group other than the oxygen atom, which is interposed. Examples of the linking group for linking the titanium atom of the metal compound to the hydrocarbon group include a phosphorus atom and a carbonyl group in addition to the oxygen atom, and include a single linking group among the groups or a combination of plural kinds of the groups.

Examples of the hydrocarbon group provided in the metal compound include a saturated aliphatic hydrocarbon group having 1 to 40 carbon atoms (preferably 1 to 20 carbon atoms, more preferably 1 to 18 carbon atoms, further preferably 4 to 12 carbon atoms, and particularly preferably 4 to 10 carbon atoms), an unsaturated aliphatic hydrocarbon group having 2 to 40 carbon atoms (preferably 2 to 20 carbon atoms, more preferably 2 to 18 carbon atoms, further preferably 4 to 12 carbon atoms, and particularly preferably 4 to 10 carbon atoms), and an aromatic hydrocarbon group having 6 to 27 carbon atoms (preferably 6 to 20 carbon atoms, more preferably 6 to 18 carbon atoms, further preferably 6 to 12 carbon atoms, and particularly preferably 6 to 10 carbon atoms).

From a viewpoint of showing the high photocatalyst function and improving dispersibility, the hydrocarbon group is preferably an aliphatic hydrocarbon group, more preferably a saturated aliphatic hydrocarbon group, and particularly preferably an alkyl group. The aliphatic hydrocarbon group may have any of a linear shape, a branched shape, and a cyclic shape. However, from a viewpoint of dispersibility, a linear shape or a branched shape is preferable.

Examples of the saturated aliphatic hydrocarbon group include a straight-chain alkyl group (a methyl group, an ethyl group, a propyl group, a butyl group, a pentyl group, a hexyl group, a heptyl group, an octyl group, a nonyl group, a decyl group, a dodecyl group, a hexadecyl group, an icosyl group, and the like); a branched alkyl group (an isopropyl group, an isobutyl group, an isopentyl group, a neopentyl group, a 2-ethylhexyl group, a tertiary butyl group, a tertiary pentyl group, an isopentadecyl group, and the like); and a cyclic alkyl group (a cyclopropyl group, a cyclopentyl group, a cyclohexyl group, a cycloheptyl group, a cyclooctyl group, a tricyclodecyl group, a norbornyl group, an adamantyl group, and the like).

Examples of the unsaturated aliphatic hydrocarbon group include an alkenyl group (a vinyl group (ethenyl group), a 1-propenyl group, a 2-propenyl group, a 2-butenyl group, a 1-butenyl group, a 1-hexenyl group, a 2-dodecenyl group, a pentenyl group, and the like); and an alkynyl group (an ethynyl group, a 1-propynyl group, a 2-propynyl group, a 1-butynyl group, a 3-hexynyl group, a 2-dodecynyl group, and the like).

The aliphatic hydrocarbon group also includes a substituted aliphatic hydrocarbon group. Examples of a substituent which may substitute the aliphatic hydrocarbon group include a halogen atom, an epoxy group, a glycidyl group, a glydoxy group, a mercapto group, a methacryloyl group, an acryloyl group, and a hydroxy group.

Examples of the aromatic hydrocarbon group include a phenylene group, a biphenylene group, a terphenylene group, a naphthalene group, and an anthracene group. The aromatic hydrocarbon group also includes a substituted aromatic hydrocarbon group. Examples of a substituent which may substitute the aromatic hydrocarbon group include a halogen atom, an epoxy group, a glycidyl group, a glydoxy group, a mercapto group, a methacryloyl group, and an acryloyl group.

A titanium compound having a hydrocarbon group is exemplified as the metal compound. Specific examples of the titanium compound include a titanate coupling agent (for example, titanate ester and phosphite of titanate ester) and titanium chelate.

Examples of the titanate coupling agent include isopropyl triisostearoyl titanate, tetraoctyl bis(ditridecyl phosphite) titanate, and bis(dioctyl pyrophosphate)oxyacetate titanate.

Examples of titanium chelate include di-i-propoxy bis (ethyl acetoacetate)titanium, di-i-propoxy bis(acetylacetonato)titanium, di-i-propoxy bis(triethanolaminate)titanium, di-i-propoxy titanium diacetate, and di-i-propoxy titanium dipropionate.

In addition to the above compounds, examples of the metal compound include titanium coupling agents such as triethanolamine titanate, titanium acetylacetonate, titanium ethyl acetoacetate, titanium lactate, titanium lactate ammonium salt, tetrastearyl titanate, isopropyl tricumyl phenyl titanate, isopropyl tri(N-aminoethyl-aminoethyl)titanate, dicumyl phenyl oxyacetate titanate, isopropyl trioctanoyl titanate, isopropyl dimethacrylisostearoyl titanate, titanium lactate ethyl ester, octylene glycol titanate, triisostearyl isopropyl titanate, isopropyl tridodecyl benzene sulfonyl titanate, tetra(2-ethylhexyl)titanate, butyl titanate dimer, isopropyl isostearoyl diacryl titanate, isopropyl tri (dioctyl phosphate)titanate, isopropyl tris(dioctyl pyrophosphate)titanate, tetraisopropyl bis(dioctyl phosphite)titanate, tetra(2, 2-diallyloxy methyl-1-butyl)bis(di-tridecyl)phosphite titanate, bis(dioctyl pyrophosphate)ethylene titanate, tetra-i-propyl titanate, tetra-n-butyl titanate, and diisostearoyl ethylene titanate.

The metal compound may be singly used or may be used in combination of two or more kinds thereof.

Characteristics of Metatitanic Acid Particle

The metatitanic acid particle according to the exemplary embodiment absorbs light having wavelengths of 450 nm and 750 nm in a visible absorption spectrum.

From a viewpoint of showing the high photocatalyst function even in the visible light region, it is preferable that the metatitanic acid particle according to the exemplary embodiment absorbs light having wavelengths of 450 nm, 600 nm, and 750 nm in the visible absorption spectrum. It is more preferable that the metatitanic acid particle absorbs light having a whole range of wavelengths of from 450 nm to 750 nm in the visible absorption spectrum. It is particularly preferable that the metatitanic acid particle absorbs light having a whole range of wavelengths of from 400 nm to 800 nm in the visible absorption spectrum.

Regarding the metatitanic acid particle, from a viewpoint of showing a high photocatalyst function even in the visible light region, in an ultraviolet-visible absorption spectrum, when absorbance at a wavelength of 350 nm is set to 1, the absorbance at a wavelength of 450 nm is preferably 0.02 or more (preferably 0.1 or more). In addition, it is more preferable that absorbance at a wavelength of 450 nm is 0.2 or more (preferably 0.3 or more), and absorbance at a wavelength of 750 nm is 0.02 or more (preferably 0.1 or more).

The "absorbing light at wavelengths of 450 nm and 750 nm" means that absorbance at a wavelength of 450 nm is 0.005 or more and absorbance at a wavelength of 750 nm is 0.005 or more in an ultraviolet-visible absorption spectrum when absorbance at a wavelength of 350 nm is set to 1.

The ultraviolet-visible absorption spectrum is measured by a method shown below. Firstly, metatitanic acid particles which are a measurement target are dispersed in tetrahydrofuran, and then are applied onto a glass substrate. Then, drying is performed at 24° C. in the air. Regarding measurement, the measurement is performed in diffuse reflection arrangement, and theoretical absorbance is obtained by Kubelka-Munk conversion. Regarding a diffuse reflection spectrum, measurement is performed in a range of wavelengths of from 200 nm to 900 nm by using reflectance, and by using a spectrophotometer (U-4100 manufactured by Hitachi High-Technologies Corporation) [measurement under measurement conditions of; a scan speed of 600 nm, a slit width of 2 nm, a sampling interval of 1 nm, and total reflectance measurement mode]. Then, Kubelka-Munk conversion is performed, thereby a visible absorption spectrum is obtained.

Regarding the metatitanic acid particle according to the exemplary embodiment, the element ratio C/Ti on the surface is from 0.2 to 1.1.

Specifically, for example, from a viewpoint of showing the high photocatalyst function even in the visible light region, the metatitanic acid particle has an element ratio C/Ti on the surface, which is preferably from 0.3 to 1.0, more preferably from 0.4 to 0.9, and particularly preferably from 0.5 to 0.8.

From a viewpoint of showing the high photocatalyst function even in the visible light region, regarding the metatitanic acid particle, the value of the element ratio O/Ti between oxygen O and titanium Ti on the surface thereof is preferably from 2.05 to 2.5, more preferably from 2.1 to 2.45, and further preferably 2.15 to 2.4.

The value of the element ratio O/Ti between oxygen O and titanium Ti on the surface of a general metatitanic acid particle which is subjected to a surface treatment with the metal compound is equal to or slightly smaller than 2.0. However, regarding the metatitanic acid particle according to the exemplary embodiment, there is a high tendency that the value of the element ratio O/Ti between oxygen O and titanium Ti on the surface of the metatitanic acid particle is from 2.05 to 2.5. It is considered that this is because the hydrocarbon group on the surface of the metatitanic acid particle is adequately carbonized. Thus, light at wavelengths of 450 nm and 750 nm is sufficiently absorbed, and the high photocatalyst function in the visible light region is shown.

Since the element ratio O/Ti is in the above range, the hydrocarbon group on the surface of the metatitanic acid particle is sufficiently carbonized. Thus, light having a wavelength of each of 450 nm and 750 nm is highly absorbed and the photocatalyst function in the visible light region is easily shown, in comparison to a case where the element ratio O/Ti is smaller than the above range. In addition, since the element ratio O/Ti is in the above range, reduction of the exposed amount of an active portion of metatitanic acid and decomposition of the hydrocarbon group caused by an excess amount of the oxygen atoms bonded to the surface are prevented and the photocatalyst function in the visible light region is easily shown, in comparison to a case where the element ratio O/Ti is greater than the above range.

The element ratio C/Ti and the element ratio O/Ti on the surface of the metatitanic acid particle are measured by a method shown below. Firstly, measurement is performed on a metatitanic acid particle which is a measurement target. The measurement is performed by using an X-ray photoelectron spectroscopy (XPS) analyzer (JPS-9000MX manufactured by JEOL Corp.) under conditions that a MgKα beam is used as an X-ray source, an acceleration voltage is set to 10 kV, and an emission current is set to 20 mA. The values of the element ratio C/Ti and the element ratio O/Ti are calculated from intensity of a peak of each element.

In the exemplary embodiment, it is preferable that the reduced amount of the element ratio C/Ti on the surface of the metatitanic acid particle in a case where the metatitanic acid particle is irradiated with an ultraviolet ray having a wavelength of 352 nm and irradiation intensity of 1.3 mW/cm$^2$ for 20 hours is from 0.1 to 0.9.

The reduced amount of the element ratio C/Ti on the surface of the metatitanic acid particle in a case where the metatitanic acid particle is irradiated with an ultraviolet ray having a wavelength of 352 nm and irradiation intensity of 1.3 mW/cm$^2$ for 20 hours is also referred to as "the reduced amount of the element ratio C/Ti by irradiation with an ultraviolet ray" or "the reduced amount of the element ratio C/Ti" below. The reduced amount of the element ratio C/Ti by irradiation with an ultraviolet ray indicates a value obtained by subtracting the element ratio C/Ti measured after irradiation with an ultraviolet ray, from the value of the element ratio C/Ti measured before the irradiation with an ultraviolet ray.

In the metatitanic acid particle which satisfies the reduced amount of the element ratio C/Ti by irradiation with an ultraviolet ray, the reduced amount of the element ratio C/Ti has a value which is greater than that of a general metatitanic acid particle subjected to a surface treatment with a metal compound or that of an untreated metatitanic acid particle. Thus, the amount of carbon in the hydrocarbon group and the like or the amount of carbon obtained by carbonizing hydrocarbon, on the surface of the metatitanic acid particle, is adequate. Light having a wavelength of each of 450 nm and 750 nm is sufficiently absorbed, and the improved photocatalyst function is shown in the visible light region. Since the hydrocarbon group and the like on the surface of the metatitanic acid particle are adequately decomposed by photocatalyst activity of the metatitanic acid particle, deterioration of a binder or a base material is prevented.

That is, since the reduced amount of the element ratio C/Ti is in the above range, decomposition and separation from the metatitanic acid particle of carbon in the hydrocarbon group and the like or carbon obtained by carbonizing hydrocarbon, on the surface of the metatitanic acid particle, which occurs by photocatalyst activity, is prevented in comparison to a case where the range of the reduced amount of the element ratio C/Ti is higher than the above range. Thus, deterioration of the photocatalyst function in the visible light region is prevented. Since the reduced amount of the element ratio C/Ti is in the above range, the amount of carbon on the surface of the metatitanic acid particle is large. Thus, sufficient absorption of light having a wavelength of each of 450 nm and 750 nm is easily obtained, and the photocatalyst function is easily obtained in the visible light region, in comparison to a case where the element ratio C/Ti is lower than the above range. Since the hydrocarbon group and the like on the surface of the metatitanic acid particle are decomposed to a certain degree, deterioration of the binder or the base material is prevented.

From a viewpoint of showing the high photocatalyst function even in the visible light region, the reduced amount of the element ratio C/Ti on the surface of the particle, which occurs by irradiation with an ultraviolet ray, is more preferably from 0.2 to 0.85, and further preferably from 0.25 to 0.8.

The volume average particle diameter of the metatitanic acid particles according to the exemplary embodiment is preferably 10 nm to 1 μm, more preferably 10 nm to 200 nm, and further preferably 15 nm to 200 nm. If the volume average particle diameter of the metatitanic acid particles is 10 nm or more, aggregation of the metatitanic acid particles is difficult, and the photocatalyst function is easily improved. If the volume average particle diameter of the metatitanic acid particles is 1 μm or less, a percentage of a specific surface area to an amount is increased, and the photocatalyst function is easily improved. Thus, if the volume average particle diameter of the metatitanic acid particles is set to be in the above range, a high photocatalyst function is easily shown in the visible light region.

The volume average particle diameter of the metatitanic acid particles is measured by using a dynamic light scattering type particle diameter measuring device (for example, NANOTRACK UPA-ST manufactured by Microtrac Bel Corporation). Regarding a measurement condition, a concentration of a sample is set to be 20%, and a measurement period is set to be 300 seconds. The dynamic light scattering type particle diameter measuring device measures a particle diameter by using a Brownian motion in dispersoid. The device irradiates a solution with a laser beam, and detects scattered light, so as to measure a particle diameter. Cumulative distribution of a volume of each particle from a small particle diameter side, in a divided particle diameter range (channel) is drawn based on particle diameter distribution which is measured by the dynamic light scattering type particle diameter measuring device. Then, a particle diameter corresponding to the accumulation of 50% is obtained as a volume average particle diameter.

Preparing Method of Metatitanic Acid Particle

A preparing method of the metatitanic acid particle according to the exemplary embodiment is not particularly limited. However, it is preferable that the preparing method includes a process of performing a surface treatment on an untreated metatitanic acid particle with a metal compound, and a process of heating the metatitanic acid particle during or after the process of performing a surface treatment on the untreated metatitanic acid particle.

Process of Performing Surface Treatment

A method of performing a surface treatment on an untreated metatitanic acid particle with a metal compound is not particularly limited. Examples of the method include a method in which a metal compound itself is directly brought into contact with an untreated metatitanic acid particle; and a method in which a treatment liquid in which the metal compound is dissolved in a solvent is brought into contact with an untreated metatitanic acid particle. Specific examples thereof include a method in which a metal compound itself or a treatment liquid is added to a dispersion in which untreated metatitanic acid particles are dispersed in a solvent, under stirring; and a method in which a metal compound itself or a treatment liquid is added (dropped, injected, or the like) to an untreated metatitanic acid particle in a state of flowing by stirring of HENSCHEL MIXER and the like. With the above methods, a reactive group (for example, a hydrolyzable group such as a halogen group and an alkoxy group) in the metal compound reacts with a hydroxyl group provided on the surface of an untreated metatitanic acid particle. Thus, the surface treatment of the untreated metatitanic acid particle is performed.

Examples of a solvent for dissolving the metal compound include an organic solvent (for example, hydrocarbon solvent, ester solvent, ether solvent, halogen solvent, and alcohol solvent), water, and a mixed solvent thereof.

Examples of the hydrocarbon solvent include toluene, benzene, xylene, hexane, octane, hexadecane, and cyclohexane. Examples of the ester solvent include methyl acetate, ethyl acetate, isopropyl acetate, and amyl acetate. Examples of the ether solvent include dibutyl ether and dibenzyl ether. Examples of the halogen solvent include 1,1-dichloro-1-fluoroethane, 1,1-dichloro-2,2,2-trifluoroethane, 1,1-dichloro-2,2,3,3,3-pentafluoropropane, chloroform, dichloroethane, and carbon tetrachloride. Examples of the alcohol solvent include methanol, ethanol, and i-propyl alcohol. Examples of the water include tap water, distilled water, and pure water.

As the solvent, a solvent such as dimethylformamide, dimethylacetamide, dimethylsulfoxide, acetic acid, and sulfuric acid may be used in addition to the above solvents.

In the treatment liquid in which the metal compound is dissolved in a solvent, concentration of the metal compound is preferably 0.05 mol/L to 500 mol/L, and more preferably 0.5 mol/L to 10 mol/L.

Regarding conditions for a surface treatment of a metatitanic acid particle with the metal compound, from a viewpoint of showing a high photocatalyst function and improving dispersibility, the following conditions may be provided. An untreated metatitanic acid particle may be subjected to a surface treatment with a metal compound which is from 10 parts by weight to 100 parts by weight (preferably from 20 parts by weight to 75 parts by weight, and more preferably from 25 parts by weight to 50 parts by weight), with respect to 100 parts by weight of the untreated metatitanic acid particle. If the amount of the metal compound is set to be 10 parts by weight or more, the high photocatalyst function is more easily shown even in the visible light region and dispersibility is easily improved. If the amount of the metal compound is set to be 100 parts by weight or less, an occurrence of a situation in which the amount of metal which is derived from the metal compound and is provided on the surface of the metatitanic acid particle becomes excessive is prevented and deterioration of the photocatalyst function caused by the surplus metal is prevented.

A temperature of the surface treatment of an untreated metatitanic acid particle with the metal compound is preferably from 15° C. to 150° C., and more preferably from 20° C. to 100° C. A surface treatment period is preferably from 10 minutes to 120 minutes, and more preferably from 30 minutes to 90 minutes.

After the surface treatment of an untreated metatitanic acid particle with the metal compound, a drying treatment may be performed. A method of the drying treatment is not particularly limited. For example, a known drying method such as a vacuum drying method and a spray drying method is applied. A drying temperature is preferably from 20° C. to 150° C.

Process of Performing Heating Treatment

The heating treatment is performed in the middle of the process of performing a surface treatment on an untreated metatitanic acid particle or performed after the process of performing a surface treatment on an untreated metatitanic acid particle.

The heating treatment may be separately performed when the untreated metatitanic acid particle is subjected to a surface treatment with the metal compound; when a drying treatment is performed after the surface treatment; or after the drying treatment. From a viewpoint of improving reactivity of the metatitanic acid particle with the metal compound before the heating treatment is performed, it is preferable that the heating treatment is separately performed when a drying treatment is performed after the surface treatment or is separately performed after the drying treatment. From a viewpoint of suitably performing the drying treatment, it is more preferable that the heating treatment is separately performed after the drying treatment.

From a viewpoint of showing a high photocatalyst function and improving dispersibility, a temperature of the heating treatment is preferably 180° C. to 500° C., more preferably 200° C. to 450° C., and further preferably 250° C. to 400° C.

From a viewpoint of showing the high photocatalyst function and improving dispersibility, a period for the heating treatment is preferably from 10 minutes to 300 minutes, and more preferably from 30 minutes to 120 minutes.

In a case where the heating treatment is performed in the middle of the process of performing a surface treatment on an untreated metatitanic acid particle, it is preferable that, firstly, the metal compound is caused to sufficiently react at the temperature of the surface treatment, and then the heating treatment is performed at the temperature of the heating treatment. In a case where the heating treatment is performed during the drying treatment after the surface treatment, the temperature of the drying treatment is used as the temperature of the heating treatment.

Since the temperature of the heating treatment is set to be from 180° C. to 500° C., metatitanic acid particles that show the high photocatalyst function even in the visible light region are effectively obtained. The reason is supposed as follows. If the heating treatment is performed at a temperature of 180° C. to 500° C., the hydrocarbon group which is provided on the surface of the metatitanic acid particle and is derived from the metal compound is adequately oxidized. Thus, some of C—C bonds or C=C bonds are changed to C—O bonds or C=O bonds.

The heating treatment is preferably performed in an atmosphere in which oxygen concentration (volume %) is from 1% to 21%. Since the heating treatment is performed in this oxygen atmosphere, the hydrocarbon group which is provided on the surface of the metatitanic acid particle and is derived from the metal compound is adequately oxidized with high efficiency. The oxygen concentration (volume %) is more preferably from 3% to 21%, and further preferably from 5% to 21%.

A method of the heating treatment is not particularly limited. A known heating method, for example, heating by an air furnace, a kiln (roller hearth kiln, shuttle kiln, or the like), a radiant heating furnace, or the like; or heating by a laser beam, an infrared ray, UV, a microwave, or the like is applied.

With the above processes, the metatitanic acid particle according to the exemplary embodiment is appropriately obtained.

Composition for Forming Photocatalyst

A composition for forming a photocatalyst according to the exemplary embodiment includes the metatitanic acid particle according to the exemplary embodiment and at least one compound selected from the group consisting of a dispersion medium and a binder.

Examples of an aspect of the composition for forming a photocatalyst according to the exemplary embodiment include a dispersion which includes the metatitanic acid particle according to the exemplary embodiment and a dispersion medium; and a composition which includes the metatitanic acid particle according to the exemplary embodiment, and an organic or inorganic binder. The dispersion may have a paste shape having high viscosity.

As the dispersion medium, water, an organic solvent, and the like are preferably used.

Examples of the water include tap water, distilled water, and pure water.

The organic solvent is not particularly limited, and for example, a hydrocarbon solvent, an ester solvent, an ether solvent, a halogen solvent, and an alcohol solvent are exemplified.

From a viewpoint of dispersion stability and storage stability, the dispersion preferably contains at least one compound selected from the group consisting of a dispersing agent and a surfactant. As the dispersing agent and the surfactant, known chemical materials are used. The dispersion may include a binder in a form of an emulsion.

The binder used in the composition is not particularly limited. Examples of the binder include an organic binder such as fluorine resin, silicone resin, polyester resin, acrylic resin, styrene resin, acrylonitrile/styrene copolymer resin, acrylonitrile/butadiene/styrene copolymer (ABS) resin, epoxy resin, polycarbonate resin, polyamide resin, polyamine resin, polyurethane resin, polyether resin, polysulfide resin, polyphenol resin, a compound thereof, and resin obtained by silicone-modifying or halogen-modifying the above resins; and an inorganic binder such as a glass, ceramic, or metal powder.

The composition for forming a photocatalyst according to the exemplary embodiment may contain other components other than the above-described components. Known additives are used as the other components, for example, a promotor, a coloring agent, a filler, an antiseptic agent, a defoaming agent, an adhesion-enhancing agent, and a thickening agent are exemplified.

The composition for forming a photocatalyst according to the exemplary embodiment may singly contain the metatitanic acid particle according to the exemplary embodiment or may contain two or more types of metatitanic acid particles.

In the composition for forming a photocatalyst according to the exemplary embodiment, the content of the metatitanic acid particle according to the exemplary embodiment is not particularly limited, and may be appropriately selected in accordance with various aspects such as a dispersion and a resin composition, and a desired amount of the photocatalyst.

A preparing method of a photocatalyst using the composition for forming a photocatalyst according to the exemplary embodiment, or a preparing method of a structure having the photocatalyst is not particularly limited, and well-known applying methods are used.

Examples of the applying method of the composition for forming a photocatalyst according to the exemplary embodiment include a spin coating method, a dip coating method, a flow coating method, a spray coating method, a roll coating method, a brush coating method, a sponge coating method, a screen printing method, and an ink jet printing method.

Photocatalyst and Structure

A photocatalyst according to the exemplary embodiment includes the metatitanic acid particle according to the exemplary embodiment.

A structure according to the exemplary embodiment contains the metatitanic acid particle according to the exemplary embodiment.

The photocatalyst according to the exemplary embodiment may be a photocatalyst formed only from the metatitanic acid particle according to the exemplary embodiment, be a photocatalyst obtained by mixing a promotor to the metatitanic acid particle according to the exemplary embodiment, or be a photocatalyst obtaining in a manner that the metatitanic acid particle according to the exemplary embodiment is solidified by an adhesive agent or a tacky agent, so as to have a desired shape.

The structure according to the exemplary embodiment preferably has the metatitanic acid particle according to the exemplary embodiment, as a photocatalyst. From a viewpoint of photocatalyst activity, the structure according to the exemplary embodiment preferably has the metatitanic acid particle according to the exemplary embodiment, on at least the surface.

The structure according to the exemplary embodiment is preferably a structure in which the metatitanic acid particle according to the exemplary embodiment is provided at least at a portion of the surface of a base material, and is preferably a structure formed by applying the composition for forming a photocatalyst according to the exemplary embodiment, to at least a portion of the surface of the base material. In the structure, the amount of the applied composition for forming a photocatalyst according to the exemplary embodiment is not particularly limited, and may be selected in accordance with a desire.

In the structure according to the exemplary embodiment, the metatitanic acid particle according to the exemplary embodiment may be adhered or fixed to the surface of the base material. However, from a viewpoint of durability of the photocatalyst, the metatitanic acid particle is preferably fixed to the surface of the base material. A fixing method is not particularly limited, and well-known fixing methods are used.

As a base material used in the exemplary embodiment, various materials are exemplified regardless of an inorganic material and an organic material. The shape of the base material is also not limited.

Preferable examples of the base material include metal, ceramic, glass, plastic, rubber, stone, cement, concrete, textile, fabric, wood, paper, and combination thereof, a stacked member thereof, and an object in which at least one coated film is provided on the surface of the above material.

Preferable examples of the base material considered from a viewpoint of a use include a building material, an exterior material, a window frame, window glass, a mirror, a table, dishes, a curtain, a lens, a prism, exterior and painting of a vehicle, facing of a mechanical device, facing of a product, a dustproof cover and painting, a traffic sign, various display devices, an advertising tower, a sound insulation wall for road, a sound insulation wall for railway, a bridge, exterior and painting of a guard rail, interior and painting of a tunnel, an insulator, a solar cell cover, a solar water heater collector cover, a polymer film, a polymer sheet, a filter, an indoor signboard, an outdoor signboard, a vehicle lighting lamp cover, an outdoor lighting equipment, an air purifier, a water purifier, medical equipment, and a nursing care product.

EXAMPLES

The present invention will be more specifically described by using examples. However, the examples do not limit the present invention. In addition, "A part" or "%" indicates a weight basis unless otherwise noted.

Example 1

Preparation of Metatitanic Acid Slurry

An anatase seed which is separately prepared and is 8% by weight with respect to $TiO_2$ in a titanyl sulfate solution in terms of $TiO_2$ is added to the titanyl sulfate solution in which $TiO_2$ concentration is 260 g/L and $Ti^{3+}$ concentration is 6.0 g/L in terms of $TiO_2$. Then, this solution is heated at a temperature higher than a boiling point, so as to perform hydrolysis of titanyl sulfate ($TiOSO_4$), and thus particulate metatitanic acid is prepared. Then, the prepared metatitanic acid particle is filtered and washed. Then, a slurry is formed, and the slurry is neutralized and washed at pH 7. In this manner, a metatitanic acid slurry having a volume average particle diameter of 40 nm is prepared.

Preparation of Metatitanic Acid Particle

A 5 N aqueous sodium hydroxide solution is added to the metatitanic acid slurry having a volume average particle diameter of 40 nm, with stirring, and thus pH thereof is set to 8.5, and the slurry is stirred and held for two hours. Then, the slurry is neutralized to pH 5.8 by using a 6 N hydrochloric acid, filtered, and washed with water. After washing, further water is added so as to form a slurry. A 6 N hydrochloric acid is added to the slurry to obtain pH 1.3, with stirring. Then, the slurry is stirred and held for three hours. 100 parts are collected as metatitanic acid, from the slurry, and are heated and held at 60° C. Then, 40 parts of isopropyl triisostearoyl titanate (PLENACT KR-TTS, manufactured by Ajinomoto Fine-Techno Co., Ltd, represented as "Isopropyl" in a table) are added while stirring. Then, the resultant is stirred and held for 30 minutes. Then, a 7 N aqueous sodium hydroxide solution is added and thus neutralization is performed to pH 7. Then, filtration and water washing are performed. The residue obtained after the filtration and water washing is spray-dried under a condition of an outer port temperature of 150° C., by an air dryer. Thus, dry powder is obtained.

A heating treatment is performed on the obtained dry powder in an electric furnace at 400° C. for one hour, and thus a metatitanic acid particle 1 is prepared.

Example 2

A metatitanic acid particle 2 is prepared in the same manner as in Example 1 except that isopropyl triisostearoyl titanate in Example 1 is changed to tetraoctyl bis(ditridecyl phosphite)titanate (PLENACT KR-46B, manufactured by Ajinomoto Fine-Techno Co., Ltd, represented as "Octyl" in the table).

Example 3

A metatitanic acid particle 3 is prepared in the same manner as in Example 1 except that isopropyl triisostearoyl titanate in Example 1 is changed to bis(dioctyl pyrophosphate)oxyacetate titanate (PLENACT KR-138S, manufactured by Ajinomoto Fine-Techno Co., Ltd, represented as "Methyl" in the table).

Example 4

A metatitanic acid particle 4 is prepared in the same manner as in Example 1 except that the added amount of isopropyl triisostearoyl titanate in Example 1 is changed from 40 parts to 50 parts.

Example 5

A metatitanic acid particle 5 is prepared in the same manner as in Example 2 except that the temperature in the electric furnace when the dried particulate powder in Example 2 is heated is changed from 400° C. to 250° C.

Example 6

A metatitanic acid particle 6 is prepared in the same manner as in Example 3 except that the temperature in the electric furnace when the dried particulate powder in Example 3 is heated is changed from 400° C. to 500° C.

Example 7

A metatitanic acid particle 7 is prepared in the same manner as in Example 1 except that the added amount of isopropyl triisostearoyl titanate in Example 1 is changed from 40 parts to 25 parts.

Example 8

A metatitanic acid particle 8 is prepared in the same manner as in Example 1 except that the added amount of isopropyl triisostearoyl titanate in Example 1 is changed from 40 parts to 75 parts.

Example 9

A metatitanic acid particle 9 is prepared in the same manner as in Example 2 except that the volume average particle diameter of the metatitanic acid slurry in Example 2 is changed from 40 nm to 15 nm.

Example 10

A metatitanic acid particle 10 is prepared in the same manner as in Example 3 except that the volume average particle diameter of the metatitanic acid slurry in Example 3 is changed from 40 nm to 980 nm.

Example 11

A metatitanic acid particle 11 is prepared in the same manner as in Example 1 except that the volume average particle diameter of the metatitanic acid slurry in Example 1 is changed from 40 nm to 10 nm.

Example 12

A metatitanic acid particle 12 is prepared in the same manner as in Example 1 except that the volume average particle diameter of the metatitanic acid slurry in Example 1 is changed from 40 nm to 1100 nm.

Comparative Example 1

A commercial anatase type titanium oxide particle ("SSP-20 (manufactured by Sakai Chemical Industry Co., Ltd.", volume average particle diameter of 12 nm)) is used as it is as a titanium oxide particle C1.

Comparative Example 2

A commercial rutile type titanium oxide particle ("STR-100N (manufactured by Sakai Chemical Industry Co., Ltd.", volume average particle diameter of 16 nm)) is used as it is as a titanium oxide particle C2.

Comparative Example 3

The commercial anatase type titanium oxide particle ("SSP-20 (manufactured by Sakai Chemical Industry Co., Ltd.", volume average particle diameter of 12 nm)) is heated at 400° C. in an electric furnace for one hour, thereby a titanium oxide particle C3 is prepared.

Comparative Example 4

The commercial rutile type titanium oxide particle ("STR-100N (manufactured by Sakai Chemical Industry Co., Ltd.", volume average particle diameter of 16 nm)) is heated at 400° C. in an electric furnace for one hour, thereby a titanium oxide particle C4 is prepared.

Comparative Example 5

A metatitanic acid particle C5 is prepared in the same manner as in Example 1 except that the added amount of isopropyl triisostearoyl titanate in Example 1 is changed from 40 parts to 5 parts.

Comparative Example 6

A metatitanic acid particle C6 is prepared in the same manner as in Example 1 except that the added amount of isopropyl triisostearoyl titanate in Example 1 is changed from 40 parts to 120 parts.

Comparative Example 7

A metatitanic acid particle C7 is prepared in the same manner as in Example 3 except that the temperature in the electric furnace when dried particulate powder in Example 3 is heated is changed from 400° C. to 600° C.

Comparative Example 8

A metatitanic acid particle C8 is prepared in the same manner as in Example 2 except that the temperature in the electric furnace when dried particulate powder in Example 2 is heated is changed from 400° C. to 160° C.

Comparative Example 9

A metatitanic acid particle C9 is prepared in the same manner as in Example 1 except that the heating treatment of the dried particulate powder in Example 1 is not performed.

Measurement

Regarding particles prepared in the respective examples, visible absorption spectrum characteristics are confirmed. As a result, the particles in Examples 1 to 12 and Comparative Examples 5 to 7 absorb light in a range of wavelengths of from 400 nm to 800 nm. Table 1 shows absorbance at a wavelength of 450 nm, absorbance at a wavelength of 600 nm, and absorbance at a wavelength of 750 nm when absorbance at a wavelength of 350 nm is set to 1 ("UV-Vis characteristics" in the table).

The element ratio C/Ti and the element ratio O/Ti on the surface of the particle by XPS, and the volume average particle diameter ("D50v" in the table) are measured in accordance with the above-described methods.

The surface of the particle prepared in each of the examples is irradiated with an ultraviolet ray having a wavelength of 352 nm and irradiation intensity of 1.3 mW/cm$^2$ at 25° C. (when the irradiation starts) for 20 hours. Then ("After irradiation with ultraviolet ray" in the table), the C/Ti element ratio on the surface of the particle by XPS is measured in accordance with the above-described method, and the reduced amount of the element ratio C/Ti by the irradiation with the ultraviolet ray is calculated.

Performance Evaluation of Metatitanic Acid Particle Photocatalyst Activity

Degradability (chromaticity variation) of an ink is evaluated as photocatalyst activity of the metatitanic acid particle in the visible light region as follows.

Metatitanic acid particles prepared in the respective examples are dispersed in water which includes 4% by weight of methanol, so as to obtain solid concentration of 2% by weight. Then, the dispersion is spray-applied onto a tile (5 cm square). Then, the tile is dried, and thus the metatitanic acid particles are uniformly adhered to the surface of the tile. Then, a diluted ink is spray-applied onto the surface thereof. Then, the tile is dried and thus a sample piece is prepared. At this time, the diluted ink is obtained in a manner that a fountain pen ink (INK-30-R manufactured by Pilot Corporation) is diluted 15 times in a methanol and water liquid mixture (methanol:water=3:5).

A test piece just after the test piece is prepared is continuously irradiated with visible light (10,000 LX (LUX)) for 2 hours by using a light emitting diode (LED) which performs irradiation with visible light having wavelengths of from 400 nm to 800 nm (an absorption wavelength region (wavelengths of from 450 nm to 550 nm) of the ink is cut by a filter). At this time, a 5-yen coin is disposed at the center portion of the irradiated surface of the test piece, and thus a blocked portion of the irradiation is formed.

Regarding the test piece just after being prepared, and the test piece after irradiation with visible light for 2 hours, hue is measured by a spectral color difference meter (RM200QC manufactured by X-Rite Inc.), and $\Delta E1$ and $\Delta E2$ calculated by the following expression are obtained. Chromaticity E is a value calculated by an expression of $E=\{(L^*)^2+(a^*)^2+(b^*)^2\}^{0.5}$. $L^*$, $a^*$, and $b^*$ indicate coordinate values in an $L^*a^*b^*$ color system.

$\Delta E1$=(chromaticity of the irradiated surface after continuous irradiation with visible light for 2 hours)−(chromaticity of the surface of a test piece just after the test piece is prepared)

$\Delta E2$=(chromaticity of the irradiation-blocked surface after continuous irradiation with visible light for 2 hours)−(chromaticity of the surface of the test piece just after the test piece is prepared)

The decoloring variation value $\Delta E=\Delta E1-\Delta E2$ is obtained from $\Delta E1$ and $\Delta E2$, and the degradability is evaluated based on $\Delta E$, as follows.

A: favorable degradability

B: slightly favorable degradability

C: poor degradability

Dispersibility 0.05 g of the metatitanic acid particle prepared in each of the examples is put into a beaker, and 40 g of methyl ethyl ketone is added. Then, particle diameter distribution after dispersing is performed for 10 minutes in an ultrasonic dispersion machine is measured by NANOTRAC UPA-ST (a dynamic light scattering type particle diameter measuring device manufactured by Microtrac Bel). Thus, distribution morphologies of volume particle diameter distribution are classified as follows.

A: one peak in the volume particle diameter distribution is provided, and dispersibility is good.

B: two peaks in the volume particle diameter distribution are provided, but the main peak value is equal to or more than 10 times the other peak value. Thus, there is no practical problem in dispersibility.

C: three peaks or more in the volume particle diameter distribution are provided, and dispersibility is poor.

TABLE 1

| | Metal compound | | | Heating temperature (° C.) | Before irradiation with ultraviolet ray | | | | | After irradiation with ultraviolet ray | | | | |
|---|---|---|---|---|---|---|---|---|---|---|---|---|---|---|
| | | | | | UV-Vis characteristics | | | | | | | | | |
| | | | | | Absorbance at wavelength of 450 nm | Absorbance at wavelength of 600 nm | Absorbance at wavelength of 750 nm | XPS | | D50v (μm) | Reduced amount of XPS | | Evaluation | |
| | Material of particle | Type | Added amount (parts by weight) | | | | | Element ratio C/Ti | Element ratio O/Ti | | Element ratio C/Ti | element ratio C/Ti | Photocatalyst activity | Dispersibility |
| Example 1 | Metatitanic acid | Isopropyl | 40 | 400 | 0.49 | 0.39 | 0.28 | 0.70 | 2.22 | 40 | 0.23 | 0.47 | A | A |
| Example 2 | Metatitanic acid | Octyl | 40 | 400 | 0.53 | 0.38 | 0.25 | 0.76 | 2.31 | 40 | 0.43 | 0.33 | A | A |
| Example 3 | Metatitanic acid | Methyl | 40 | 400 | 0.56 | 0.42 | 0.27 | 0.63 | 2.26 | 40 | 0.26 | 0.37 | A | A |
| Example 4 | Metatitanic acid | Isopropyl | 50 | 400 | 0.52 | 0.43 | 0.31 | 0.52 | 2.37 | 40 | 0.35 | 0.17 | A | A |
| Example 5 | Metatitanic acid | Octyl | 40 | 250 | 0.33 | 0.25 | 0.17 | 1.07 | 2.07 | 40 | 0.19 | 0.88 | B | A |
| Example 6 | Metatitanic acid | Methyl | 40 | 500 | 0.36 | 0.27 | 0.19 | 0.45 | 2.08 | 40 | 0.22 | 0.23 | B | A |
| Example 7 | Metatitanic acid | Isopropyl | 25 | 400 | 0.39 | 0.28 | 0.16 | 0.23 | 2.07 | 40 | 0.11 | 0.12 | B | B |
| Example 8 | Metatitanic acid | Isopropyl | 75 | 400 | 0.62 | 0.45 | 0.28 | 0.90 | 2.36 | 40 | 0.21 | 0.69 | A | A |
| Example 9 | Metatitanic acid | Octyl | 40 | 400 | 0.59 | 0.42 | 0.25 | 0.58 | 2.15 | 15 | 0.35 | 0.23 | A | A |

TABLE 1-continued

| | Metal compound | | | | Before irradiation with ultraviolet ray | | | | | | After irradiation with ultraviolet ray | | Evaluation | |
|---|---|---|---|---|---|---|---|---|---|---|---|---|---|---|
| | | | | | UV-Vis characteristics | | | | | | Reduced amount | | | |
| | | | | Heating temperature (° C.) | Absorbance at wavelength of 450 nm | Absorbance at wavelength of 600 nm | Absorbance at wavelength of 750 nm | XPS | | | XPS | of | | |
| | Material of particle | Type | Added amount (parts by weight) | | | | | Element ratio C/Ti | Element ratio O/Ti | D50v (μm) | Element ratio C/Ti | element ratio C/Ti | Photo-catalyst activity | Dispersibility |
| Example 10 | Metatitanic acid | Methyl | 40 | 400 | 0.54 | 0.40 | 0.23 | 0.76 | 2.38 | 980 | 0.38 | 0.38 | A | B |
| Example 11 | Metatitanic acid | Isopropyl | 40 | 400 | 0.60 | 0.45 | 0.30 | 0.82 | 2.12 | 10 | 0.34 | 0.48 | A | A |
| Example 12 | Metatitanic acid | Isopropyl | 40 | 400 | 0.52 | 0.36 | 0.20 | 0.92 | 2.47 | 1100 | 0.54 | 0.38 | B | A |
| Comparative Example 1 | Anatase type titanium oxide | None | None | None | 0.00 | 0.00 | 0.00 | 0.19 | 2.00 | 12 | 0.16 | 0.03 | C | C |
| Comparative Example 2 | Rutile type titanium oxide | None | None | None | 0.00 | 0.00 | 0.00 | 0.19 | 1.94 | 16 | 0.16 | 0.03 | C | C |
| Comparative Example 3 | Anatase type titanium oxide | None | None | 400 | 0.00 | 0.00 | 0.00 | 0.16 | 1.97 | 12 | 0.16 | 0.00 | C | C |
| Comparative Example 4 | Rutile type titanium oxide | None | None | 400 | 0.00 | 0.00 | 0.00 | 0.16 | 2.01 | 16 | 0.16 | 0.00 | C | C |
| Comparative Example 5 | Metatitanic acid | Isopropyl | 5 | 400 | 0.02 | 0.01 | 0.01 | 0.18 | 2.02 | 40 | 0.16 | 0.02 | C | C |
| Comparative Example 6 | Metatitanic acid | Isopropyl | 120 | 400 | 0.65 | 0.48 | 0.30 | 1.35 | 2.65 | 40 | 1.35 | 0.00 | C | B |
| Comparative Example 7 | Metatitanic acid | Methyl | 40 | 600 | 0.08 | 0.05 | 0.02 | 0.17 | 2.03 | 40 | 0.10 | 0.07 | C | C |
| Comparative Example 8 | Metatitanic acid | Octyl | 40 | 160 | 0.02 | 0.01 | 0.00 | 1.23 | 2.02 | 40 | 0.29 | 0.94 | C | B |
| Comparative Example 9 | Metatitanic acid | Isopropyl | 40 | None | 0.00 | 0.00 | 0.00 | 1.27 | 2.01 | 40 | 1.22 | 0.05 | C | A |

It is apparent that photocatalyst activity in the examples is better than that in the comparative examples, from the above results. Thus, it is apparent that the examples show a high photocatalyst function even in the visible light region in comparison to the comparative examples. It is apparent that the examples also ensure dispersibility.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A metatitanic acid particle, comprising:
   a core particle containing metatitanic acid (TiO(OH)$_2$) as a major component; and
   a metal compound, which includes a titanium metal atom and a carbon atom, bonded to a surface of the core particle via an oxygen atom,
   wherein an element ratio (C/Ti) between carbon and titanium on a surface of the metatitanic acid particle is in a range of 0.2 to 1.1; and
   the metatitanic acid particle has an absorption at a wavelength of each of 450 nm and 750 nm in a visible absorption spectrum.

2. The metatitanic acid particle according to claim 1, wherein the metatitanic acid particle has an absorption in a whole range of wavelengths of from 400 nm to 800 nm in the visible absorption spectrum.

3. The metatitanic acid particle according to claim 1,
wherein an element ratio (O/Ti) between oxygen and titanium on the surface of the metatitanic acid particle is in a range of 2.05 to 2.50.

4. The metatitanic acid particle according to claim 1,
wherein the carbon atom is included in a saturated aliphatic hydrocarbon group having 1 to 20 carbon atoms, an unsaturated aliphatic hydrocarbon group having 2 to 20 carbon atoms, or an aromatic hydrocarbon group having 6 to 20 carbon atoms.

5. The metatitanic acid particle according to claim 1,
wherein the carbon atom is included in a saturated aliphatic hydrocarbon group having 1 to 20 carbon atoms.

6. The metatitanic acid particle according to claim 1,
wherein the carbon atom is included in a saturated aliphatic hydrocarbon group having 4 to 10 carbon atoms.

7. The metatitanic acid particle according to claim 1,
wherein a volume average particle diameter of the metatitanic acid particles is in a range of 10 nm to 1 μm.

8. The metatitanic acid particle according to claim 1,
wherein an element ratio (O/Ti) between oxygen and titanium on the surface of the metatitanic acid particle is in a range of 2.10 to 2.40.

9. The metatitanic acid particle according to claim 1,
wherein an element ratio (C/Ti) between carbon and titanium on the surface of the metatitanic acid particle is in a range of 0.3 to 1.0.

10. A composition for forming a photocatalyst, comprising:
the metatitanic acid particle according to claim 1; and
at least one compound selected from the group consisting of a dispersion medium and a binder.

11. A photocatalyst comprising:
the metatitanic acid particle according to claim 1.

* * * * *